United States Patent [19]
Schwartz et al.

[11] Patent Number: 5,900,933
[45] Date of Patent: May 4, 1999

[54] APPARATUS FOR MEASURING PARTICLE DIMENSIONS IN FLUIDS

[75] Inventors: Friedel Herbert Schwartz; Michael Braun, both of Dusseldorf, Germany

[73] Assignee: Messtechnik Schwartz GmbH, Dusseldorf, Germany

[21] Appl. No.: 09/089,478

[22] Filed: Jun. 2, 1998

[30] Foreign Application Priority Data

Jun. 6, 1997 [DE] Germany .................. 197 23 999

[51] Int. Cl.[6] .......................... G01N 15/02; G01N 21/00
[52] U.S. Cl. ...................... 356/336; 356/335; 356/337; 356/338; 356/342
[58] Field of Search .................... 356/336, 335, 356/337, 338, 342

[56] References Cited

U.S. PATENT DOCUMENTS

| 3,858,851 | 1/1975 | Ogle ........................................ 356/102 |
| 5,266,798 | 11/1993 | Borden et al. ........................... 356/338 |
| 5,748,311 | 5/1998 | Hamann et al. ......................... 356/336 |

FOREIGN PATENT DOCUMENTS 0 289 200 A2  11/1988  European Pat. Off. .
2 243 681     11/1991  United Kingdom .

*Primary Examiner*—Robert H. Kim
*Assistant Examiner*—Roy M. Punnoose
*Attorney, Agent, or Firm*—Milton Oliver; Ware, Fressola, Van Der Sluys & Adolphson LLP

[57] ABSTRACT

Apparatus for analysing particle dimensions of particles contained in a fluid with an illuminating device for illuminating the particles to be analysed, incorporates a source for generating light. An optical system is disposed between the source and the fluid with a fluid-side window transparent to the light, which focusses the light on the opposite side of the window in the fluid and displaces the focal point along a path running around a center line of the apparatus. A detector device detects the light scattered by the particles and generates an electric signal dependent on the scattered light. A housing is provided between the fluid and the illuminating device and/or the detector device, with an analysis unit for determining the size and/or the size distribution of the particles. A device for setting the distance between the focal point and the window can be dispensed with if the optical system incorporates at least one stationary interface relative to the housing when it is in operation, which is disposed non-rotationally symmetrical in relation to the center line of the apparatus.

10 Claims, 2 Drawing Sheets

APPARATUS FOR MEASURING PARTICLE DIMENSIONS IN FLUIDS

BACKGROUND TO THE INVENTION

The present invention relates to an apparatus for analysing particle dimensions of particles contained in a fluid.

Known apparatus for analysing particle dimensions of particles contained in a fluid use a focussed light beam to sweep the particle to be measured. The time is then measured in which the respective particle interrupts the light beam during transmissive measurement or reflects the light beam during reflective measurement. The determination of the particle dimensions from the above-mentioned time is possible only if the relative speed of particles in relation to the light beam is known precisely. For this purpose, the focal point is displaced along a circular path or a zig-zag path at a speed which is great compared with the speed of the individual particles.

In the case of large particle concentrations it is necessary to bring the focus sufficiently close to the fluid-side window that the extinction of the light beam in the fluid remains small. On the other hand the focal point must maintain a minimum distance from the fluid-side window which is greater than the radius of the greatest particles to be measured. Otherwise the particle would not be determined in its full size.

Such particle measuring apparatus is disclosed in U.S. Pat. No. 3,858,851, in which the scanning laser beam is displaced on a circular path by incorporating a plane-parallel plate obliquely into the beam path and rotating it about an axis running parallel with the direction of the incident laser beam. This generates a parallel displacement of the laser beam and hence the desired path. The focal point of the device lies within the fluid and does not have to be set separately, because the fluid is intrinsically transparent.

In the particle measuring apparatus disclosed in GB-A-2243681 the incident laser beam falls through a rotating prism, and the circular path of the focal point is generated in this way. Particles are analysed on a specimen slide with this measuring instrument. In addition the particles have to lie in the area of the focal point of the optical device. The holder of the specimen slide can be displaced for this purpose.

Another apparatus for reflective operation is known from EP-A-289200. With this apparatus, which can be immersed in a fluid as a probe, a focal point rotating along a circular path is likewise generated. For the setting of the distance between the fluid-side window and the focal point a separate focussing device is provided, which in the course of operation sets the reflected signal to a maximum achievable amplitude level as a function of the properties of the fluid. However, the difficulty arises in practice that the focussing device necessitates certain structural measures and in addition has to be activated by the process control system. The focussing device therefore leads to a complicated layout of the apparatus and to a further measurement and control variable which has to be monitored or generated.

SUMMARY OF THE INVENTION

The present invention provides apparatus for analysing particle dimensions of particles contained in a fluid, which comprises:

(a) an optical system disposed between the source and the fluid with a fluid-side window transparent to the light, in which the optical system focusses the light substantially on the farther side of the window in the fluid and displaces the focal point along a path, (b) a detector device for detecting the light scattered by the particles and for generating an electric signal dependent on the scattered light, (c) a housing provided between the fluid and the illuminating device and/or the detector device, (d) an analysis unit for determining the size and/or the size distribution of the particles, (e) an illuminating device for illuminating the particles to be analysed, which incorporates a source for generating light, in which the optical system incorporates at least one stationary interface relative to the housing when it is in operation, which is disposed non-rotationally symmetrical in relation to the centre line of the apparatus.

The apparatus of the present invention has the advantage that it enables particle dimensions in fluids to be measured for reflective operation in which the distance of the focal point from the fluid-side window does not have to be set even with high particle concentrations.

Because the optical system incorporates at least one face rim stationary relative to the housing when it is in operation, which face rim is disposed non-rotationally symmetrical in relation to the centre line of the apparatus, the focal point migrates to and fro on its path in the fluid between a position directly adjacent to the fluid-side window and a position removed from the fluid-side window. In this way, without a setting of the distance, at least parts of the path of the focal point are led along at a distance from the window such that favourable conditions for the various measurement requirements are obtained. It is in particular not necessary, if the transparency of the medium varies in time or if the concentration of the particles to be analysed varies in time, to control the distance of the focal point from the fluid-side window. Although the path of the focal point leads with optically dense media in some cases to an extinction of the measured signal, the quantity of measured signals capable of being analysed is in any case sufficiently great that the statistical significance of the measured signal is achieved without difficulty, and a good result can be achieved even with only partial analysis of the measured signals. The advantage of not requiring and not having to activate a focussing device with the measuring apparatus far outweighs the slightly higher work-load in evaluating the signals. It is in addition advantageous if the interface is substantially even and inclined at an angle relative to the centre line of the apparatus. Simple geometric relationships are obtained as a result. A further simple embodiment is obtained if the interface is the fluid-side surface of the window, it being preferable if the fluid-side surface of the window is formed plane. It can also be provided, however, that the interface is a surface of a prism which is disposed in the beam path between the light source and the fluid-side window. If the focal length of the optical system is changed by the prism in such a way that the focal point varies in its depth of penetration. If the interface, as mentioned above, represents the fluid-side surface of the window, the length of the optical path is varied across the path of the focal point. Both possibilities lead to the advantages according to the invention.

Further advantages accrue if the angular position of the optical system relative to the window is recorded and analysed. The additional information, which correlates with the distance of the focal point from the window, represents a dimension not included to date in the measured values.

INTRODUCTION TO THE DRAWINGS

FIG. 1 shows the fluid-side top of a measuring apparatus, in which the interface with the fluid is disposed obliquely relative to the centre line, FIG. 2 a fluid-side top according to FIG. 1 with a prism in the beam path.

DESCRIPTION OF PREFERRED EMBODIMENTS

Figure 1:
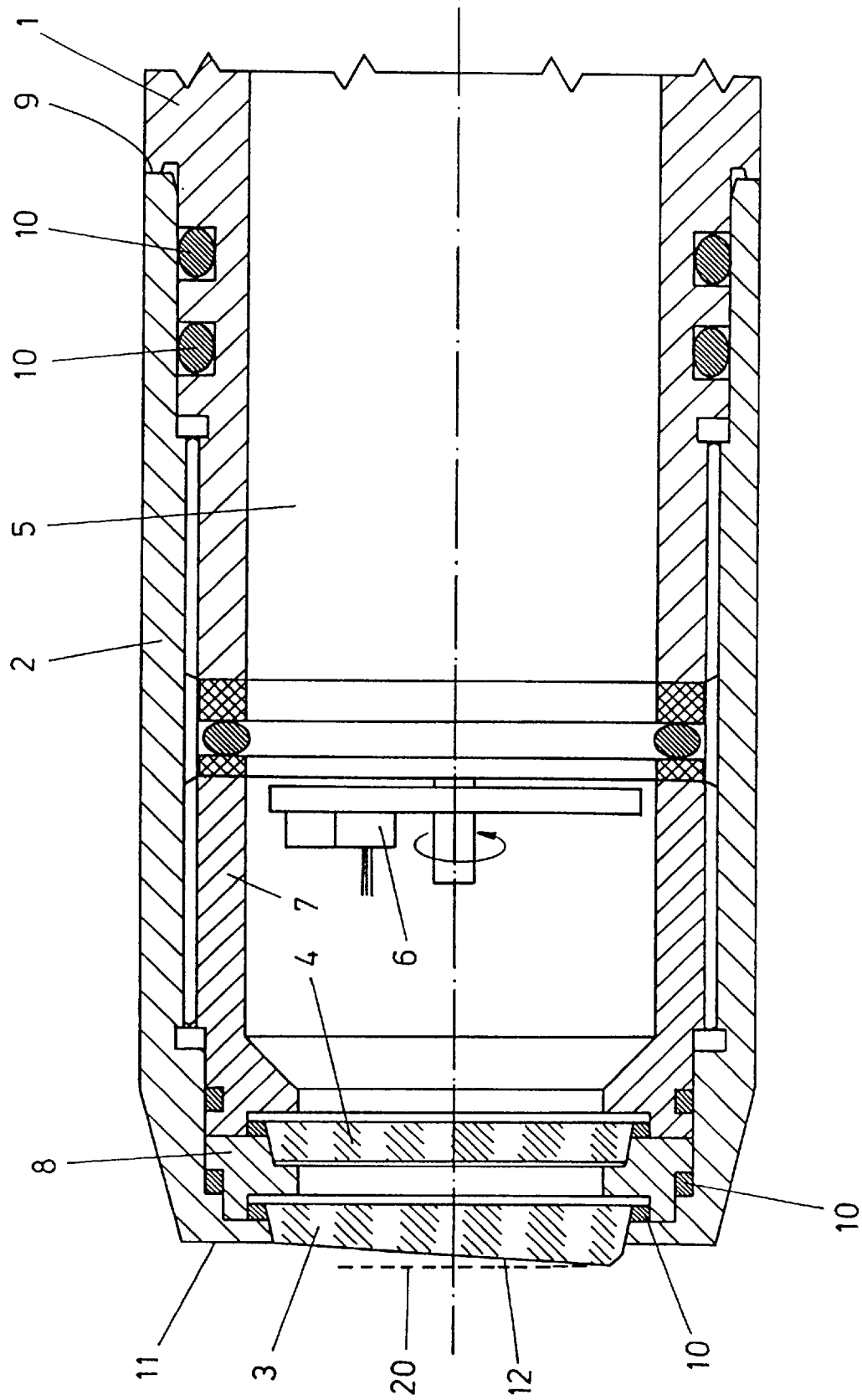

FIG. 1 shows a probe according to the invention with a basic body 1, an outer sleeve 2 as well as an outer window 3 and an inner window 4 in a cross-section. The basic body 1 surrounds an interior space 5 of substantially round cross-section, in which a merely indicated optical device 6 is so disposed that it can rotate around the centre line of the probe. There butts against the optical system 6 in the direction of the windows 3 and 4 a roughly tube-shaped adapter 7, which supports the window 4. There butts against the window 4 and the tubular member 7 in the fluid-side direction a further, tube-shaped adapter 8, which supports the fluid-side window 3. The sleeve 2 surrounds the basic body 1, the optical system 6 as well as the adapters 7 and 8 and the windows 3 and 4 in the outward direction. At the same time the sleeve 2 has substantially the same diameter as the basic body 1, against which the sleeve 1 butts in a ring-shaped band 9. The adapter 7 is together with the components adjacent to it screwed into the sleeve 2, while the sleeve 2 is in turn screwed onto the basic body 1. The tightness relative to the fluid to be measured is ensured by O-rings 10.

At its free end the sleeve 2 is conically bevelled and ends in an end surface 11 which is circular and moreover of smaller diameter than the diameter of the sleeve 2. The end surface 11 of the sleeve 2 surrounds a plane surface 12 of the window 3, which plane surface 12 lies oblique to the centre line as an optical interface with the fluid.

Figure 2:
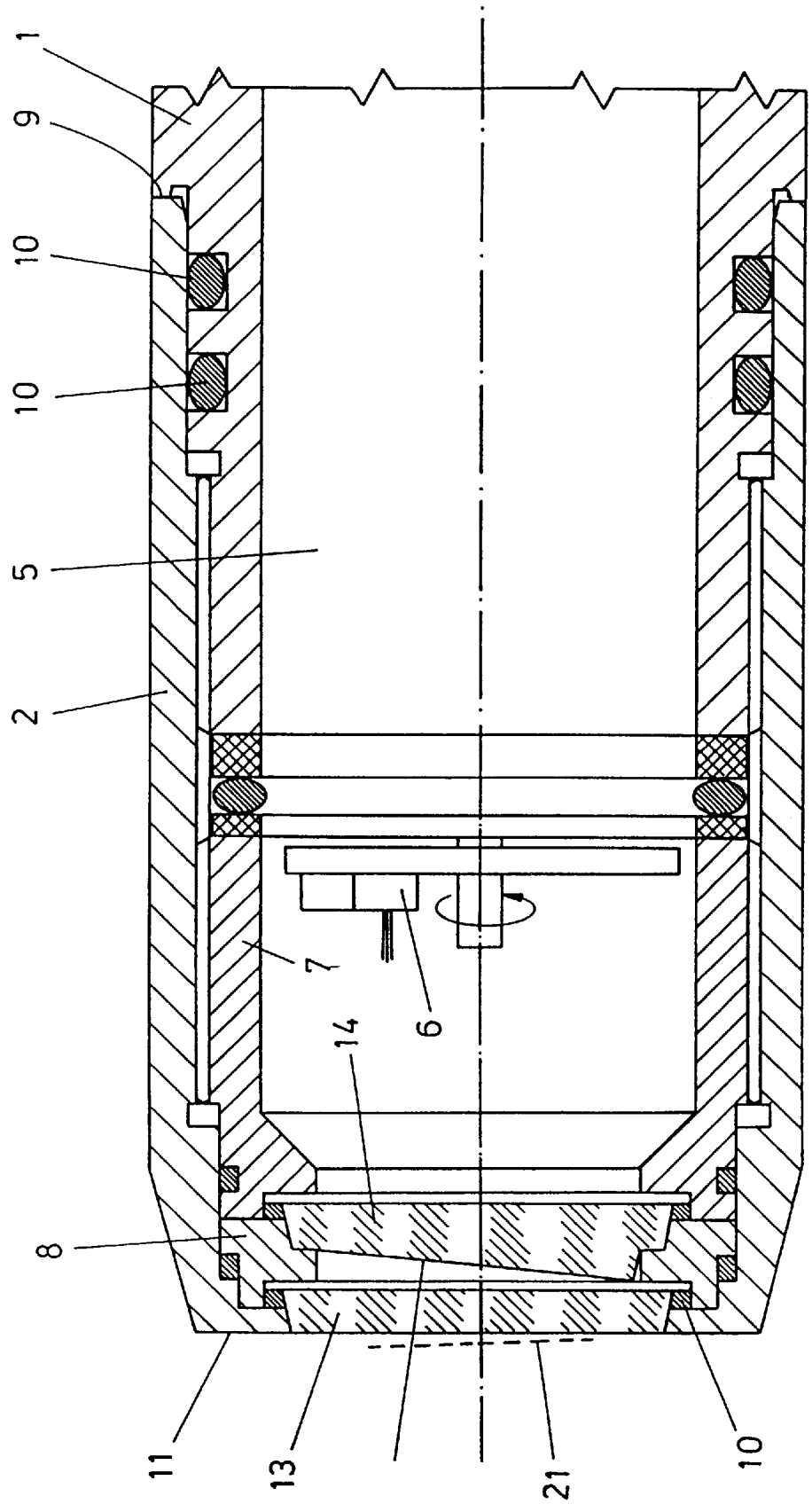

FIG. 2 shows a probe in cross-section, which corresponds substantially to the probe according to FIG. 1. The same components are marked with the same reference symbols.

In this embodiment an outer plane-parallel window 13 and an inner prismatic window 14 are provided, as a window disposed in the probe, with a surface 15 disposed obliquely to the centre line. The window 14 is plane at its surface facing the probe inside 5.

In practice the optical system 6 generates a laser beam oriented parallel with the centre line of the probe head, which laser beam is displaced relative to the centre line and passes through the windows 3 and 4 or 13 and 14 and is focussed outside the probe head in the fluid. Particles are illuminated in said focal point, which back-scatter the light. The back-scattered light passes through the windows 3 and 4 or 13 and 14 again and is detected by the optical system 6 and analysed with series-connected electronics.

In the embodiment according to FIG. 1 the optical system 6 forms the focal point outside the probe head in the fluid, wherein due to the rotary movement of the optical system 6 substantially a circular path 20 of the focal point is obtained, which runs in a plane at right angles to the centre line of the apparatus. The circular path 20 is in FIG. 1, by virtue of the obliquely positioned outer surface 12 of the window 3, removed further from the window than at the side shown at the bottom of FIG. 1. A continuous variation of the distance between the focal point and the window surface in the course of operation is obtained as a result. A setting of the distance between the window and the focal point is not necessary. Different areas of the circular path 20 can be analysed for various measurement conditions (concentration, mean particle size, opacity of the fluid). A further method of determining the connection between the respective circular path section and the measured signal generated is also possible here if there is added to the measured signal as a parameter the position of the optical system the moment the data are recorded. In this way, for example, measured values on the transparency of the fluid can also be obtained in addition to the particle size.

Whereas in the embodiment according to FIG. 1 the focal length of the optical system remains substantially constant, with the embodiment according to FIG. 2 the focal length changes and hence the distance of the focal point from the optical system 6. This can be attributed to the fact that the focussed, converging light beams issuing from the optical system 6 have to travel along paths of different length in the optically dense medium in the window 15. A variation in the distance of the focal point from the front surface of the window 13 consequently results, which leads to a path 21 running obliquely to the centre line. The metrological effect of the obliquely running path 21 corresponds to that in the embodiment according to FIG. 1. There are here path sections of the focal point which lie closer to the window and are therefore suitable for determining particle sizes in not very transparent fluids, while the path sections further removed from the window 13 are suitable for determining the dimensions of larger particles.

Depending on the field of application, the angle of the obliquely disposed interface 12 or 15 can be selected so that particular distance ranges are passed through. For example, the distances can be varied between 0 and 1000 $\mu$m. It even does not do any harm if parts of the path of the focal point run inside the fluid-side window. A measured signal is then simply not present in said areas. This loss of the measured signal can be tolerated with relatively large particle concentrations, because the quantity of measured particles within the remaining areas of the path is in general sufficiently large that a good statistical significance of the measured signal is obtained. The absence of the measured signal could in this case even be used for calibration purposes, because the correlation between the measured signal and the position of the optical system 6 along its circular path can be used to obtain information as to where the focal point enters the window and exits again. The position adopted by the optical system 6 in which the distance of the focal point from the fluid-side window is equal to zero is therefore also known.

Although in the embodiments only one optical interface oblique to the centre line has been shown in each case, it is obvious that several faces of this kind can also be formed. In addition, faces which differ from the flat configuration shown can also be selected.

What is claimed is:

1. Apparatus for analysing particle dimensions of particles contained in a fluid, which comprises:
   (a) an optical system disposed between the source and the fluid with a fluid-side window transparent to the light, in which the optical system focusses the light substantially on the farther side of the window in the fluid and displaces the focal point along a path,
   (b) a detector device for detecting the light scattered by the particles and for generating an electric signal dependent on the scattered light,
   (c) a housing provided between the fluid and the illuminating device and/or the detector device,
   (d) an analysis unit for determining the size and/or the size distribution of the particles,
   (e) an illuminating device for illuminating the particles to be analysed, which incorporates a source for generating light, in which the optical system incorporates at least one stationary interface relative to the housing when it is in operation, which is disposed non-rotationally symmetrical in relation to the centre line of the apparatus.

2. Apparatus as claimed in claim 1, in which the path runs around a centre line of the apparatus.

3. Apparatus as claimed in claim 1, in which the interface is substantially flat and inclined at an angle relative to the centre line of the apparatus.

4. Apparatus as claimed in claim 1, in which the interface is the fluid-side surface of the window.

5. Apparatus as claimed in claim 1, in which at least the fluid-side surface of the fluid-side window is plane.

6. Apparatus as claimed in claim 1, in which the interface is a surface of a prism which is disposed in the beam path between the source and the fluid-side window.

7. Apparatus as claimed in claim 1, which includes means for determining the position of the focal point on the path.

8. Apparatus as claimed in claim 1, in which the analysis unit is in at least one mode of operation installed so as to analyse the detected signals as a function of the position of the focal point along its path.

9. Apparatus as claimed in claim 1, in which the path of the focal point touches the fluid-side surface of the window.

10. Apparatus as claimed in claim 1, in which the path of the focal point runs in certain sections within the fluid-side window.

* * * * *